(12) United States Patent
Speck et al.

(10) Patent No.: US 10,874,868 B1
(45) Date of Patent: Dec. 29, 2020

(54) ANTENNA ASSEMBLY

(71) Applicant: Micron Medical LLC, Boca Raton, FL (US)

(72) Inventors: Benjamin Speck, Boca Raton, FL (US); Graham Patrick Greene, Boca Raton, FL (US)

(73) Assignee: Micron Medical LLC, Boca Raton, FL (US)

( * ) Notice: Subject to any disclaimer, the term of this patent is extended or adjusted under 35 U.S.C. 154(b) by 0 days.

(21) Appl. No.: 16/835,403

(22) Filed: Mar. 31, 2020

(51) Int. Cl.
*A61N 1/40* (2006.01)
*A41D 1/00* (2018.01)

(52) U.S. Cl.
CPC ............. *A61N 1/40* (2013.01); *A41D 1/005* (2013.01)

(58) Field of Classification Search
None
See application file for complete search history.

(56) References Cited

U.S. PATENT DOCUMENTS

| | | |
|---|---|---|
| 8,849,412 B2 | 9/2014 | Perryman et al. |
| 9,254,393 B2 | 2/2016 | Perryman et al. |
| D752,761 S | 3/2016 | Perryman et al. |
| 9,421,367 B1 * | 8/2016 | Wendell ............... A61N 1/0408 |
| 9,522,270 B2 | 12/2016 | Perryman et al. |
| 10,056,688 B2 | 8/2018 | Andresen et al. |
| 10,058,705 B2 | 8/2018 | Andresen et al. |
| 2016/0136438 A1 * | 5/2016 | Perryman ............. A61N 1/321 |
| | | 607/60 |

* cited by examiner

*Primary Examiner* — Brian T Gedeon
(74) *Attorney, Agent, or Firm* — Banner & Witcoff, Ltd.

(57) ABSTRACT

An antenna assembly includes a band having an interior layer and an exterior layer, and configured to be wrapped around a portion of a user's body such that the interior layer faces a user's body. A locking assembly includes a first locking portion and a second locking portion, the first and second locking portions being configured to engage one another to secure the band about the user's body. An antenna is positioned between the interior and the exterior layers. A docking port is positioned between the interior and the exterior layers. A circuitry housing is received in the docking port and includes a printed circuit board and a battery. A connector has a first end connected to the printed circuit board and a second end connected to the antenna.

19 Claims, 7 Drawing Sheets

ANTENNA ASSEMBLY

TECHNICAL FIELD

This disclosure relates to an antenna assembly, and more particularly, an antenna assembly that can be worn on the body of a user.

BACKGROUND

Neural modulation of neural tissue in the body by electrical stimulation has become an important type of therapy for chronic disabling conditions, such as pain, movement control, involuntary movement, dystonia, urinary and fecal incontinence, sexual dysfunction, vascular insufficiency, heart arrhythmia and a multitude of other neural based compromised modalities. Electrical stimulation of the nerve bundles has been used commercially in the United States since the 1970s. Implanted electrodes are used to pass pulsatile electrical currents of controllable frequency, pulse width and amplitudes to surrounding tissue once implanted in the body. The electrical field may cross over certain neural elements, typically axons, and can selectively activate varying diameters of axons, with positive therapeutic benefits. A variety of therapeutic intra-body electrical stimulation techniques may be utilized to treat neuropathic conditions utilizing implanted electrodes connected to a source of power, such as a battery powered implanted pulse generator or an embedded wireless receiver, in the spinal column or surrounding areas, including the dorsal horn, dorsal root ganglia, dorsal roots, dorsal column fibers and peripheral nerve bundles leaving the dorsal column or brain, such as vagus-, occipital-, trigeminal, hypoglossal-, sacral-, unlar-, median, radial-, cluneal, ilioguinal, tibial, and coccygeal nerves.

A transmitter with an antenna may be worn on the body of the user to deliver radio frequency ("RF") energy to a wireless receiver housed in an implanted stimulation device in the body.

SUMMARY

In general, this disclosure relates to a wearable antenna assembly concept utilizing improved comfort, fit, ergonomics, and aesthetics that can deliver RF energy to an implanted stimulation device via an internal receiver.

In accordance with one aspect, an antenna assembly includes a band having an interior layer and an exterior layer, and configured to be wrapped around a portion of a user's body such that the interior layer faces a user's body. A locking assembly includes a first locking portion and a second locking portion, the first and second locking portions being configured to engage one another to secure the band about the user's body. An antenna is positioned between the interior and the exterior layers. A docking port is positioned between the interior and the exterior layers. A circuitry housing is received in the docking port and includes a printed circuit board and a battery. A connector has a first end connected to the printed circuit board and a second end connected to the antenna.

In accordance with another aspect, an antenna assembly includes a band having an interior fabric layer and an exterior fabric layer, and configured to be wrapped around a portion of a user's body such that the interior fabric layer faces a user's body. A locking assembly includes a first locking portion and a second locking portion, one of the first locking portion and the second locking portion being a hook fastener, and the other of the first locking portion and the second locking portion being a loop fastener. An antenna is positioned between the interior and the exterior layers. A docking port is positioned between the interior and the exterior layers. A circuitry housing received in the docking port and having an interior cavity. A printed circuit board includes a control circuit and seated in the interior cavity of the circuitry housing. An alarm is seated in the interior cavity of the circuitry housing. A battery is seated in the interior cavity of the circuitry housing. A control panel is positioned at an open end of the interior cavity of the circuitry housing and has a plurality of interface buttons to control at least one of: an amplitude setting, a pulse width setting, a frequency setting, and a preset programs setting. A connector has a first end connected to the printed circuit board and a second end connected to the antenna.

In accordance with a further aspect, an antenna assembly includes a band having an interior stretchable layer and an exterior stretchable layer, and configured to be wrapped around a portion of a user's body such that the interior stretchable layer faces a user's body. A locking assembly includes a hook fastener on one of the interior stretchable layer and the exterior stretchable layer and a loop fastener on the other of the interior stretchable layer and the exterior stretchable layer. An antenna includes a plurality of arms and is positioned between the interior and exterior stretchable layers. A docking port is positioned between the interior and the exterior layers, with a first surface irregularity being formed on an interior surface of the docking port. A circuitry housing us received in the docking port, and has a base, a cover secured to the base, a mating second surface irregularity formed on an exterior surface of the circuitry housing, and an interior cavity. A printed circuit board includes a control circuit and is seated in the interior cavity of the circuitry housing. A piezo alarm is seated in the interior cavity of the circuitry housing. A rechargeable battery has a charging port and is seated in the interior cavity of the circuitry housing. A control panel is positioned at an open end of the interior cavity of the circuitry housing and has a plurality of interface buttons to control at least one of: an amplitude setting, a pulse width setting, a frequency setting, and a preset programs setting. A connector has a first end connected to the printed circuit board and a second end connected to the antenna.

Additional aspects, configurations, embodiments and examples are described in more detail below.

DESCRIPTION OF DRAWINGS

Certain manufacturing techniques and manufactured devices are described below with reference to the accompanying figures.

The figures referred to above are not drawn necessarily to scale and should be understood to provide representative examples, illustrative of the principles involved. Some features of the antenna assembly depicted in the drawings have been enlarged or distorted relative to others to facilitate explanation and understanding. The same reference numbers are used in the drawings for similar or identical components and features shown in various alternative embodiments. Antenna assemblies as disclosed herein would have configurations and components determined, in part, by the intended application and environment in which they are used.

DETAILED DESCRIPTION

Certain improvements to wearable antenna assemblies are described herein. The term "approximately" as used herein is meant to mean close to, or about a particular value, within the constraints of sensible commercial engineering objectives, costs, manufacturing tolerances, and capabilities in the field of antenna assembly manufacturing and use. Similarly, the term "substantially" as used herein is meant to mean mostly, or almost the same as, within the constraints of sensible commercial engineering objectives, costs, manufacturing tolerances, and capabilities in the field of antenna assembly manufacturing and use.

FIGS. 1-4 show an example of an antenna assembly 100 configured to transmit RF energy to an implanted stimulation device, including, for example, neurostimulators and pacemakers. The implanted devices require a programmed electrical waveform and power source in order to provide the therapy to the patient. The implanted devices may have a wireless receiver designed to mate with the external RF energy source provided by antenna assembly 100.

As seen in FIGS. 1-4, antenna assembly 100 may include a band 102 configured to be wrapped around a portion of a user's body. Band 102 may be formed of a first interior layer 104 and a second exterior layer 106 secured to interior layer, and may have a first end 108 and an opposed second end 110.

In certain embodiments, interior layer 104 and exterior layer 106 may be formed of a flexible or semi-rigid material to provide flexibility for band 102, and improve its ability to conform to the irregular shapes of various portions of a user's body when band 102 is wrapped about a portion of the user's body. Band 102 may be wrapped about the user's body such that interior layer 104 faces the user's body. In some embodiments, when band 102 is wrapped about a portion of the user's body, interior layer 104 may directly contact the user's body. In other embodiments, band 102 may be wrapped about a portion of the user's body covered by an article of clothing, e.g., a shirt or a sock, and in such a case interior layer 104 would directly contact the fabric or other material of which the article of clothing is formed.

Band 102 may be stretchable so that it can be wrapped around a portion of the user's body to a desired tightness. Once band 102 is removed from the user's body, it can return to its original shape. It is to be appreciated that in certain embodiments the entirety of band 102 may be formed of a stretchable material, while in other embodiments one or more segments of band 102 may formed of a stretchable material while other segments are formed of a non-stretchable material.

The support and flexibility of band 102 can help protect the components of antenna assembly 100 during sudden movements and/or vibrations caused by movement of the user, such as drops or falls, or due to external forces such as motor vehicle vibrations, for example.

By ensuring that antenna assembly 100 can easily conform to the irregular shapes of various portions of the user's body, antenna assembly 100 may have improved comfort, fit, and ergonomics, as well as improved aesthetics. The improved comfort, fit, ergonomics, and aesthetics may in turn encourage users to use antenna assembly 100 and the stimulation device to which it is connected more often.

Interior layer 104 and exterior layer 106 may be formed of a fabric material or a breathable, antimicrobial supportive material such as neoprene, compressed foam, an elastomer, rubber, or polyurethane. Other suitable materials for interior layer 104 and exterior layer 106 will become readily apparent to those skilled in the art.

Interior layer 104 may be secured to exterior layer 106 by any suitable fastening means. For example, interior layer 104 may be secured to exterior layer 106 by an adhesive, such as epoxy or glue. In other embodiments, interior layer 104 may be secured to exterior layer 106 with stitching, or bonding. Other suitable means of securing interior layer 104 to exterior layer 106 will become readily apparent to those skilled in the art.

Band 102 may include a locking assembly 112 that can be used to secure band 102 about a user's body. In certain embodiments, locking assembly 112 may include a first locking portion 114 and a second locking portion 116. First locking portion 114 may be positioned on an exterior surface 118 of exterior layer 106, and may be positioned proximate first end 108 of band 102. Second portion 116 may be positioned on an exterior surface 120 of interior layer 104, and may be positioned proximate second end 110 of band 102.

First locking portion 114 and second locking portion 116 may engage one another and cooperate to act as a unified fastener, securing band 102 in a fixed position. In certain embodiments, one of first locking portion 114 and second locking portion 116 may be a hook fastener, with the other of first locking portion 114 and second locking portion 116 being a mating loop fastener. In the illustrated embodiment, first locking portion 114 is a hook fastener and second locking portion 116 is a mating loop fastener.

In other embodiments, first locking portion 114 and second portion of locking assembly 112 may be formed as snap-fit fasteners, buttons, interlocking elements with mating geometries such as projections that are press fit into mating cavities, temporary adhesives, clips, safety pins, zippers, magnets, or any other releasable mechanical elements. Other suitable fasteners for locking assembly 112 will become readily apparent to those skilled in the art In some embodiments, band 102 may be custom formed to fit various parts of the body, including the ankle, lower leg, knee, upper leg, waist, chest, neck, shoulder, upper arm, elbow, lower arm, and wrist, for example. The shape of band 102 may be contoured to accommodate the variable diameter of any body part and maintain the intended position while the user is in motion. It is to be appreciated that band 102 could be wrapped about any portion of a user's body.

Figure 4:
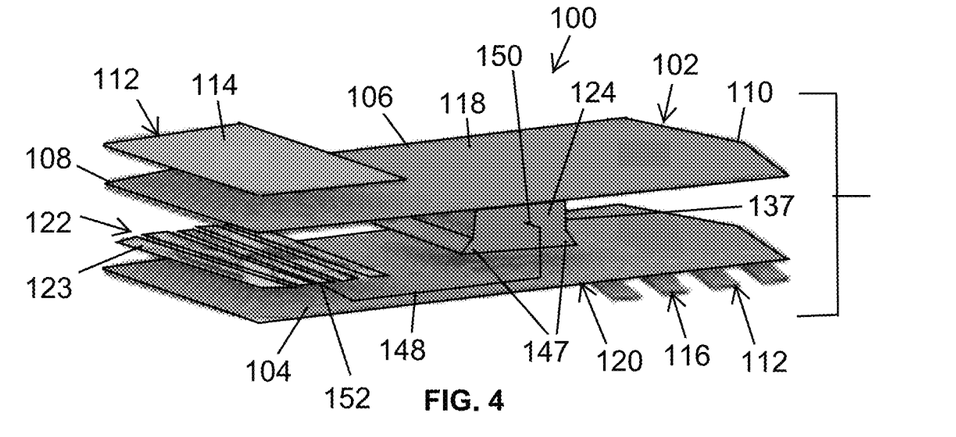
FIG. 4 is an exploded view of the antenna assembly of FIG. 1.

Band 102 may include an antenna 122 positioned between interior layer 104 and exterior layer 106 such that antenna 122 is embedded within an interior of band 102. In certain embodiments, antenna 122 may include a plurality of arms 123 that may extend substantially parallel to one another. Antenna 122 may serve to transmit RF energy to a stimulator implanted within the user's body, for example. Antenna 122 may have a characteristic frequency with a range from approximately 800 MHz to approximately 1 GHz, and in certain embodiments may operate at 869 MHz or at 915 MHz, depending on the country in which antenna assembly 100 operates. In certain embodiments, antenna 122 may be a directional patch antenna, while in other embodiments antenna 122 may be a monopole, dipole, vagi, whip, or horn antenna.

Antenna 122 may be formed of a flexible material so as to conform to the portion of the user's body about which band 102 is wrapped. Antenna 122 may also be designed to match the permittivity of body tissue in order to efficiently transfer RF energy into the user's body. In certain embodiments, antenna 122 may be formed of copper, silver, conductive ink, polyimide, polyester, or a fabric material.

Band 102 may include a housing or docking port 124 positioned between interior layer 104 and exterior layer 106. Docking port 124 may define an interior cavity 126 therein and have an open end 128 exposing interior cavity 126 to an exterior of docking port 124. Docking port 124 may be formed of a plastic, such as acrylonitrile butadiene styrene ("ABS"), polyethylene, polypropylene, nylon, semi-soft polyurethanes or silicones, or from rigid or flexible metals. Other suitable materials for docking port 124 will become readily apparent to those skilled in the art, given the benefit of this disclosure.

Figure 1:
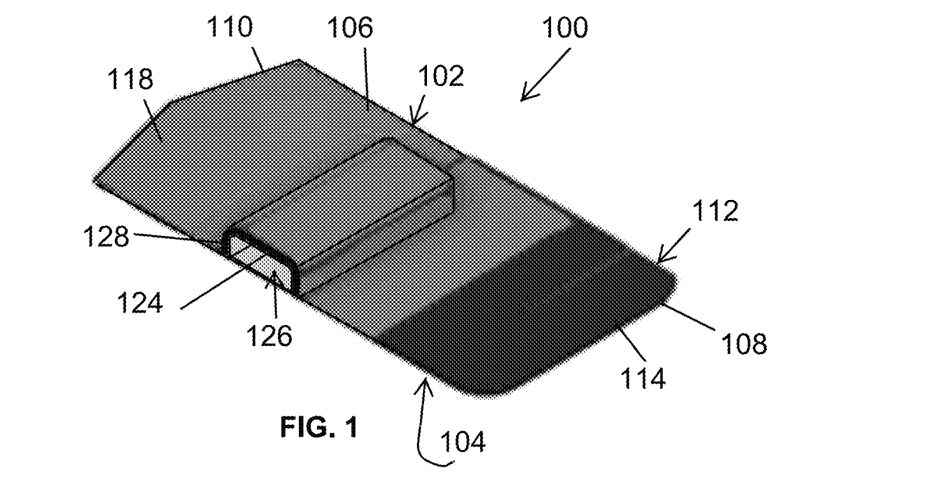
FIG. 1 is a top perspective view of an antenna assembly.
Figure 2:
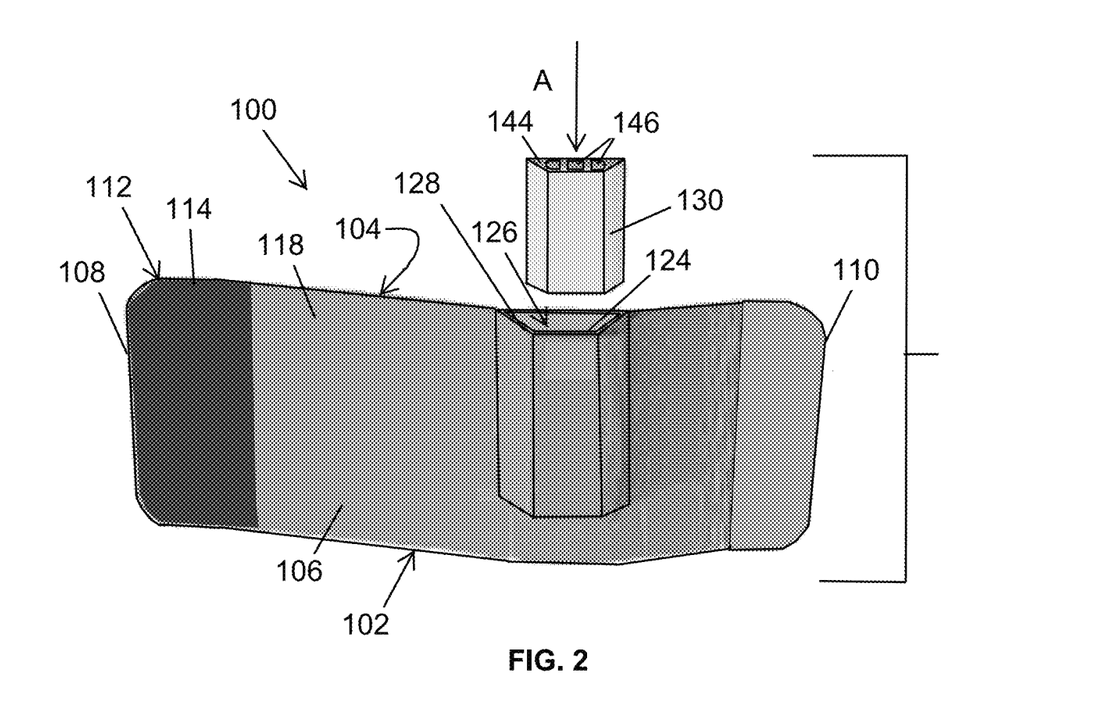
FIG. 2 is a top perspective view of the antenna assembly of FIG. 1, shown with a circuitry housing being inserted into a docking port of the antenna assembly.
Figure 3:
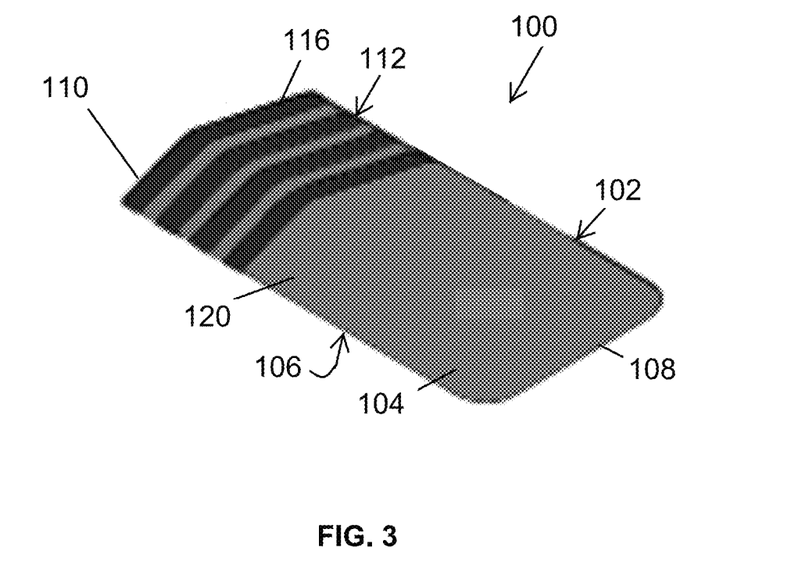
FIG. 3 is a bottom perspective view of the antenna assembly of FIG. 1.

As seen in FIG. 1, exterior layer 106 may be stretched so as to cover docking port 124 when interior layer 104 and exterior layer 106 are secured together. Docking port 124 may be secured to exterior layer 106 and interior layer 104 of band 102 by adhesive or bonding, for example. Open end 128 of docking port 124 may be exposed when interior layer 104 and exterior layer 106 are secured together, thereby allowing a circuitry housing 130 to be received in interior cavity 126.

Figure 5:
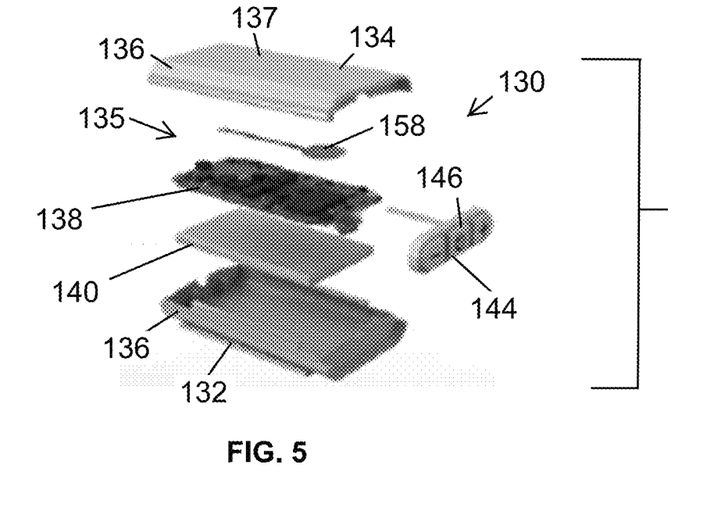
FIG. 5 is an exploded view of the circuitry housing of the antenna assembly of FIG. 1.

As seen in FIG. 5, circuitry housing 130 may include a base 132 and a cover 134 secured to base 132, and base 132 and cover 134 may define an interior cavity 135 within circuitry housing 130. Circuitry housing 130 may serve to protect components housed therein from mechanical, electrical, or environmental stresses that may result in damage to such components.

One or both of base 132 and cover 134 may define sidewalls 136 surrounding interior cavity 135 of circuitry housing 130. Base 132 and cover 134 may be releasably secured to one another with snap-fit mechanical connections or other suitable releasable fasteners, allowing access to interior cavity 135 of circuitry housing 130 in order to repair and/or replace components housed therein. Base 132 and cover 134 may be formed of plastic, metal, rubber, or fabric, for example.

As described above, and seen in FIG. 2, circuitry housing 130 may be received in interior cavity 126 of docking port 124. By making the geometry of the exterior surface 137 of circuitry housing 130 mate with the geometry of interior cavity 126 of docking port 124, circuitry housing 130 can be self-aligned as it is received in interior cavity 126, improving the ease of use of antenna assembly 100 and decreasing the possibility of wear and tear on the components of antenna assembly 100. In certain embodiments, circuitry housing 130 and docking port 124 may have mating geometries such as surface irregularities, e.g., mating slots and grooves, to facilitate the docking of circuitry housing 130 into docking port 124 and ensuring their alignment, as well as the alignment of the components of circuitry housing 130. Thus, circuitry housing 130 may be easily inserted into and removed from docking port 124, thereby facilitating cleaning or replacement of band 102, and replacement, repair, or upgrading of the components of circuitry housing 130.

A printed circuit board ("PCB") 138 with circuitry thereon, including an RF transmitter, may be positioned within circuitry housing 130. PCB 138 may include a control circuit that manages the electrical operations of antenna assembly 100 including, for example, its charging cycle, RF transmission, and feedback communication.

In certain embodiments, PCB 138 may be configured to communicate wirelessly with remote devices, e.g., computers or smartphones, by way of Bluetooth, WIFI, or RF, or any other suitable wireless communication protocol. Such wireless communication may be used to send programming information, extract usage logs and trending data, inform the user of device status or health parameters, load or upgrade firmware to the RF transmitter of PCB 138, and enable direct communication or troubleshooting with the end user.

In certain embodiments, PCB 138 may be shielded so as to be protected from RF interference. In certain embodiments, the RF shielding geometry for PCB 138 may be designed to allow for a wireless communication signal to be transmitted out of circuitry housing 130 while preventing unwanted spurious emissions.

Figure 7:
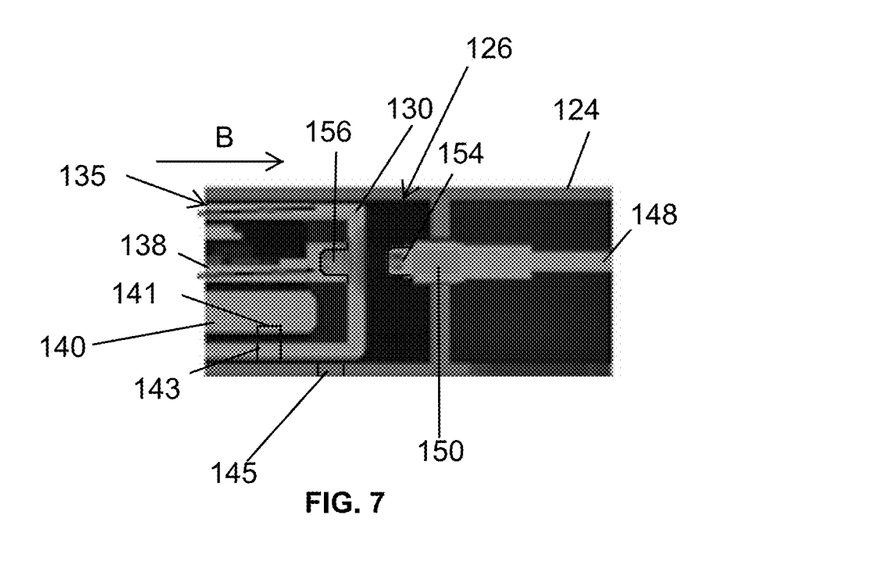
FIG. 7 is an elevation view, partially broken away, of the circuitry housing of the antenna assembly of FIG. 1 being inserted into the docking port.
Figure 8:
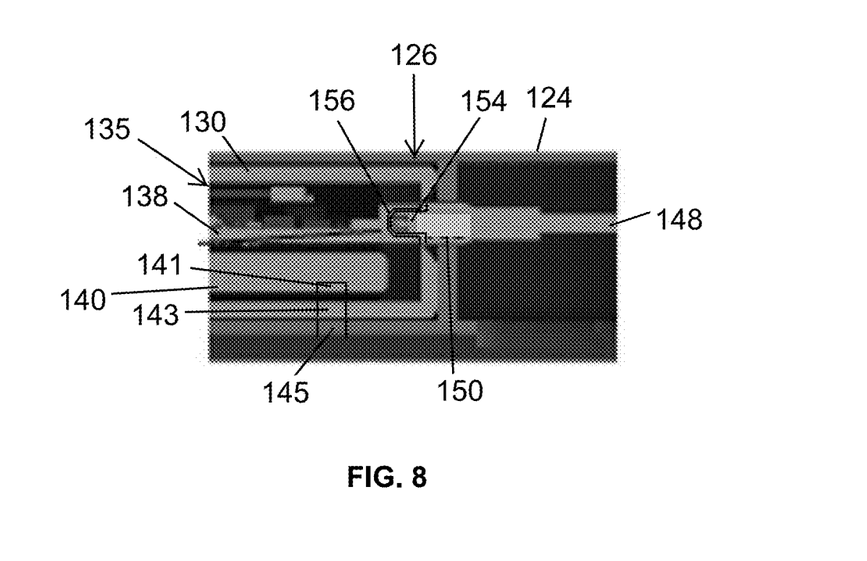
FIG. 8 is an elevation view, partially broken away, showing the circuitry housing of the antenna assembly of FIG. 1 fully inserted into the docking port.

A battery 140 may be positioned in circuitry housing 130 to provide power to the control circuitry of PCB 138. In certain embodiments, battery 140 may be a replaceable battery such as a lithium-ion, lithium polymer, nickel cadmium, or nickel metal-hydride battery, for example. In other embodiments, battery 140 may be a rechargeable battery, in which case a charging port 141, as seen in FIGS. 7-8, may be provided, which may be accessed through an aperture 143 formed in circuitry housing 130 and a mating aperture 145 formed in docking port 124. Charging port 141 may be for example, a microUSB port, a lightning port, a barrel type port, or any other suitable charging port. It is to be appreciated that battery 140 could also be charged through charging port 141 when battery 140 is removed from circuitry housing 130.

Figure 6:
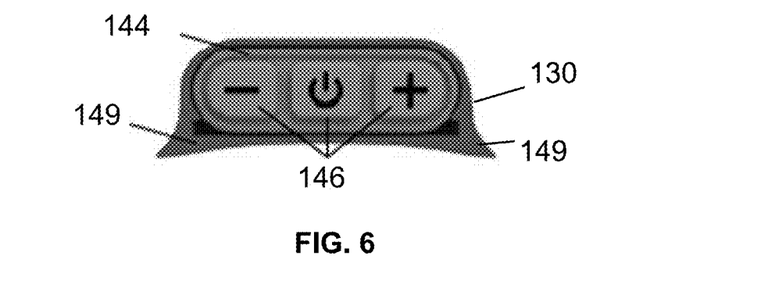
FIG. 6 is an end view of the circuitry housing of the antenna assembly of FIG. 1.

A control panel 144 may be provided at one end of circuitry housing 130, as seen in FIG. 6, such that control panel 144 is exposed when circuitry housing 130 is received in interior cavity 126 of docking port 124. Control panel 144 may include one or more interface buttons 146 to control the operation of antenna assembly 100. For example, interface buttons 146 may control an amplitude setting, a pulse width setting, a frequency setting, and a preset program setting for antenna assembly 100.

As noted above, the geometry of circuitry housing 130 and docking port 124 may be configured in a mating fashion to facilitate insertion of circuitry housing 130 into docking port 124 in the proper alignment. In certain embodiments, an interior surface of docking port 124 may have a first surface irregularity such as a recess 149, or a pair of recesses 147 as seen in FIG. 4, and exterior surface 137 of circuitry housing 130 may have a mating second surface irregularity such as a projection 149, or a pair of projections 149, as seen in FIG. 6. Projections 149 of circuitry housing 130 may be received in the corresponding mating recesses 147 of docking port 124 to ensure the mating engagement of circuitry housing 130 and docking port 124.

It is to be appreciated that the first surface irregularity 147 of docking port 124 could be a projection while the second surface irregularity 149 of circuitry housing 130 could be a mating recess. Further, it is to be appreciated that first surface irregularity 147 of docking port 124 and second surface irregularity 149 of circuitry housing 130 could take any form. Additionally, it is to be appreciated that any number of first surface irregularities 147 could be formed on docking port 124, while a corresponding number of second surface irregularities 149 could be formed on circuitry housing 130.

A connector 148 may have a first end 150 thereof connected to PCB 138, as illustrated in FIGS. 7-8, and a second end 152 thereof connected to antenna 122, as illustrated in FIG. 4. Connector 148 may be a cable, such as a coaxial cable, for example. In other embodiments, connector 148 could take the form of a microstrip, a printed circuit board, a stripline, a waveguide, or any other suitable conduit or cable, or any other means capable of transmitting RF energy from PCB 138 to antenna 122.

Connector 148 may be positioned such that it extends substantially parallel or substantially perpendicular to arms 123 of antenna 122. It is to be appreciated that conductors of connector 148, both signal and ground, should not cross over to the opposite side of antenna arms 123 (signal to ground or vice versa).

In certain embodiments, connector 148 is positioned between interior layer 104 and exterior layer 106 of band 102 such that when interior layer 104 and exterior layer 106 are secured together. Connector 148 is embedded within band 102, protecting connector 148 from external forces and possible damage, as well as providing strain relief for connector 148. In other embodiments, connector 148 could be positioned within either of interior layer 104 or exterior layer 106.

It is to be appreciated that either or both of interior layer 104 and exterior layer 106 of band 102 may have reinforced areas or additional supportive material (not shown) where connector 148 is positioned within band 102 in order to provide additional strain relief as well as protection from wear and tear. For example, either or both of interior layer 104 and exterior layer 106 may include supportive material that includes grains, fibers, or cross-sectional patterns running along the length (vertical or horizontal) of the layer, and which provides reinforcement and/or strain relief for connector 148 at critical zones (e.g. bend zones) of interior layer 104 and exterior layer 106.

As illustrated in FIGS. 7-8, first end 150 of connector may have a plug 154, and first end 150 may be fixed or secured to docking port 124 such that plug 154 extends into interior cavity 126 of docking port 124. PCB 138 may have a mating receptacle 156 configured to receive plug 154. As circuitry housing 130 is inserted into interior cavity 135 of docking port 124, it is guided rearwardly such that plug 154 may engage with receptacle 156, establishing the connection between PCB 138 and antenna 122.

It is to be appreciated that docking port 124 may be spaced from antenna 122 so that interaction between the field radiated by the antenna 122 with components on PCB 138 (e.g., traces on its RF transmitter) can be minimized.

An alarm 158 may be positioned within circuitry housing, as seen in FIG. 5, and may provide notifications to the end user. Alarm 158 may be connected to PCB 138 and provide the user with feedback regarding operation of antenna assembly 100 and/or the stimulation device with which antenna assembly 100 is communicating. Alarm 158 may be a piezoelectric or piezo alarm that provides haptic feed back to the user through vibrations, a speaker, an LED light, a fiber optic element, or variable temperature element, for example.

Figure 9:
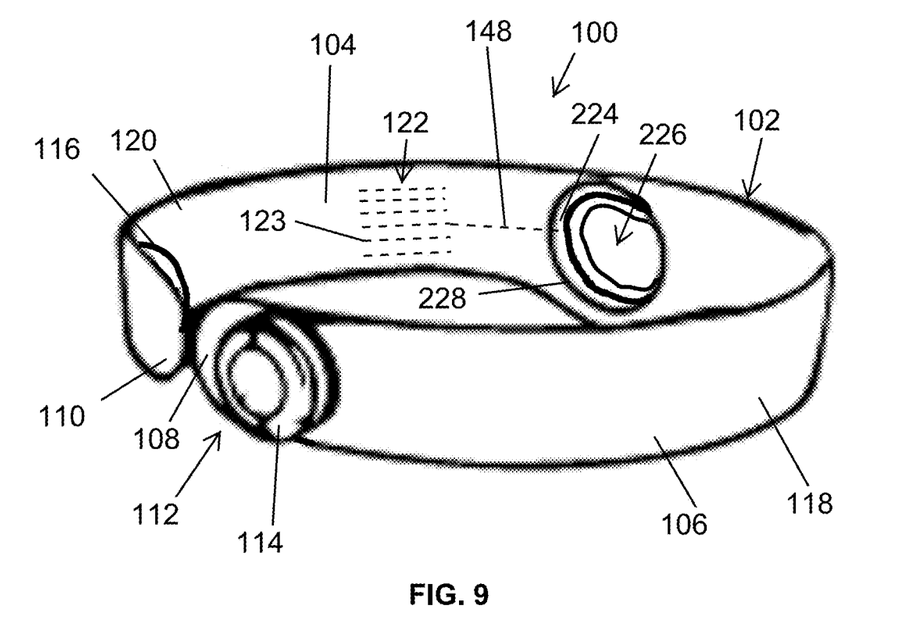
FIG. 9 is a perspective view of an alternative embodiment of the antenna assembly of FIG. 1.
Figure 10:
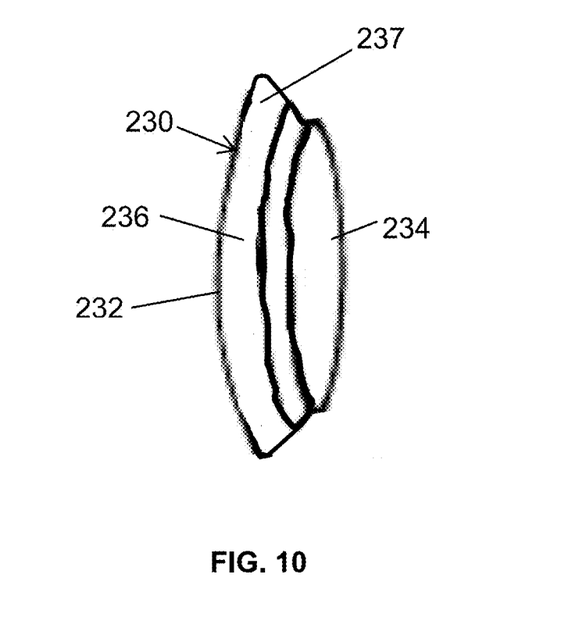
FIG. 10 is a perspective view of a circuitry housing to be inserted into the docking port of the antenna assembly of FIG. 9.

Another embodiment of antenna assembly 100 is seen in FIGS. 9-10, where a docking port 224 is shown with a circular configuration, and a circuitry housing 230 is shown with a mating circular configuration. Circuitry housing 230 may have a base 232, a cover 234, and sidewalls 236. An interior cavity (not visible here) of circuitry housing 230 may house components such as PCB 138, battery 140, and alarm 158. The circular geometry of the exterior surface 237 of circuitry housing 230 may mate with the circular geometry of interior cavity 226 of docking port 224 so that circuitry housing 230 can be self-aligned as it is received in interior cavity 226.

Circuitry housing 230 may be inserted into interior cavity 226 of docking port 224 through open end 228. As shown in FIG. 9, antenna 122, its arms 123, and connector 148 are all embedded in band 102 between interior layer 104 and exterior layer 106. In this embodiment, first locking portion 114 and second locking portion 116 of locking assembly 112 may take the form of snap-fit fasteners.

Figure 11:
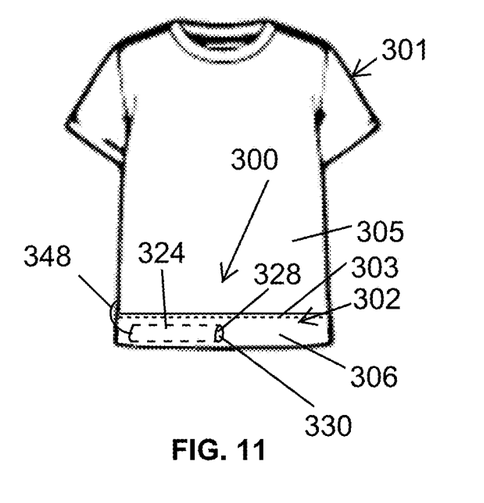
FIG. 11 is a front elevation of an article of apparel shown with an alternative embodiment of the antenna assembly of FIG. 1.
Figure 12:
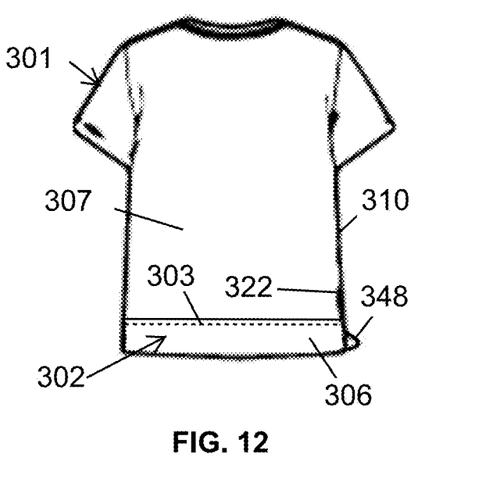
FIG. 12 is a rear elevation of the article of apparel of FIG. 11.

Another embodiment is shown in FIGS. 11-14, where an antenna assembly 300 is positioned within an article of clothing in the form of a shirt 301. In this embodiment, a docking port 324 is captured within a band 302, taking the form of a hem 302 of shirt 301. Hem 302 may be secured to shirt 301 with stitching 303, for example. As shown in FIG. 11, docking port 324 is seated within hem 302 on a front 305 of shirt 301, with the front 305 of shirt 301 forming the interior layer of the band, and the upwardly turned portion of hem 302 forming the exterior layer of the band. A connector 348 may traverse within hem 302 to a rear 307 of shirt 301 where it may be connected to an antenna 322 that extends upwardly along a seam 310 of shirt 301.

Figure 13:
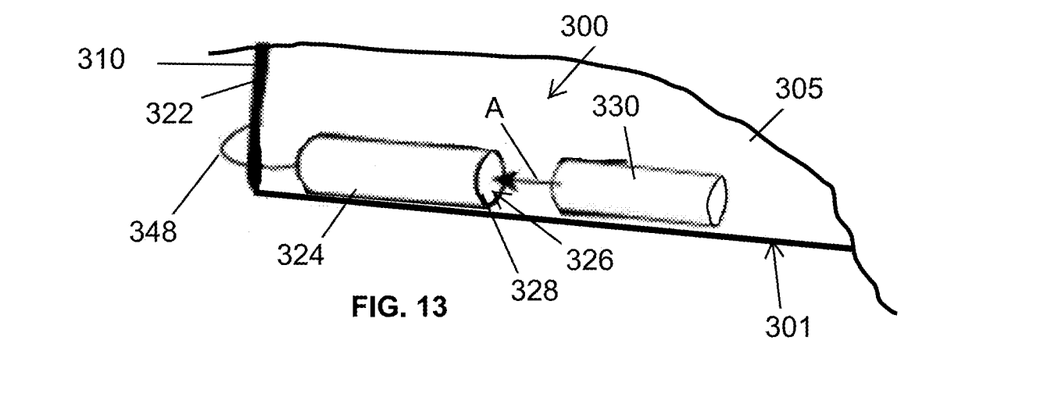
FIG. 13 is a perspective view of the circuitry housing of the antenna assembly of FIG. 11 being inserted into the docking port.
Figure 14:
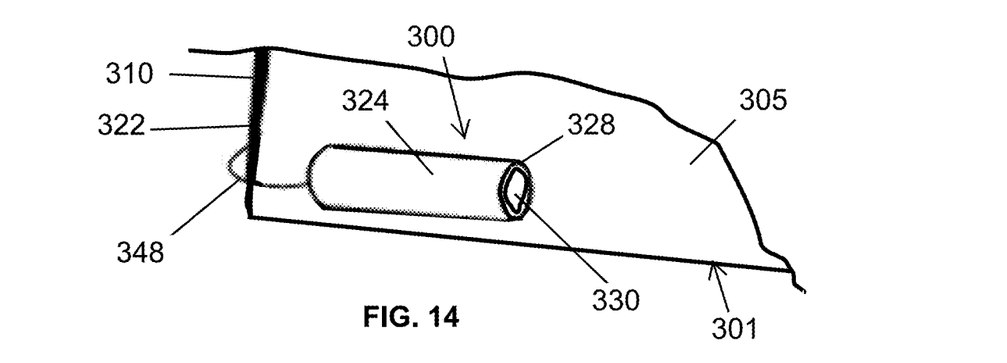
FIG. 14 is a perspective view of the circuitry housing of the antenna assembly of FIG. 11 fully inserted into the docking port.

In this embodiment, circuitry housing 330 and docking port 324 each may have a cylindrical configuration. As illustrated in FIG. 13, the mating cylindrical shapes allow circuitry housing 330 to inserted in the direction of arrow A through open end 328 into an interior cavity 126 of docking port 324.

Figure 15:
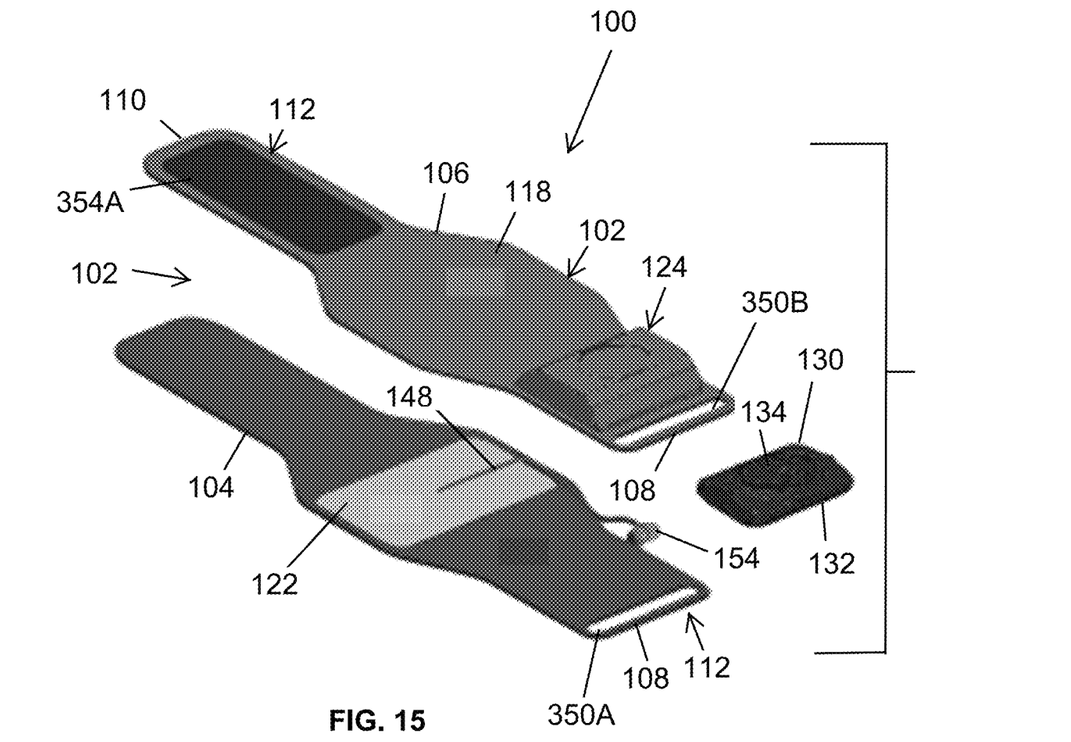
FIG. 15 is an exploded perspective view another alternative embodiment of the antenna assembly of FIG. 1.

Another embodiment of antenna assembly 100 is illustrated in FIG. 15. In this embodiment, locking assembly 112 includes a loop 350 with a first portion 350A formed at first end 108 of interior layer 104 and a second portion 350B formed at first end 108 of exterior layer 306. Locking assembly 112 also includes a hook and loop fastener 354 with a first portion 354A positioned on exterior layer 106 proximate second end 110, and a second portion positioned on interior layer 104 (not visible here). To secure band 102, second end 110 can be threaded through loop 350 and wrapped back on itself, at which point the portions of hook and loop fastener 354 can be matingly engaged, thereby securely fastening band 102 about a portion of the user's body.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. Terms "top," "upper," "bottom," "lower," "left," "right," and the like, as used herein, are intended for illustrative purposes only and do not limit the embodiments in any way. When used in description of a method or process, the term "providing" (or variations thereof) as used herein means generally making an article available for further actions, and does not imply that the entity "providing" the article manufactured, assembled, or otherwise produced the article. Nothing in this specification should be construed as requiring a specific three dimensional orientation of structures in order to fall within the scope of this invention, unless explicitly specified by the claims. Additionally, the term "plurality," as used herein, indicates any number greater than one, either disjunctively or conjunctively, as necessary, up to an infinite number. Accordingly, while the specific embodiments have been illustrated and described, numerous modifications come to mind without significantly departing from the spirit of the invention and the scope of protection is only limited by the scope of the accompanying claims.

What is claimed is:

1. An antenna assembly comprising:
   a band including an interior layer and an exterior layer, and configured to be wrapped around a portion of a user's body such that the interior layer faces a user's body;
   a locking assembly including a first locking portion and a second locking portion, the first and second locking portions configured to engage one another to secure the band about the user's body;
   an antenna positioned between the interior and the exterior layers;
   a docking port positioned between the interior and the exterior layers;
   a circuitry housing received in the docking port and including a printed circuit board and a battery;
   a connector having a first end connected to the printed circuit board and a second end connected to the antenna;
   a first surface irregularity on an interior surface of the docking port; and
   a mating second surface irregularity on an exterior surface of the circuitry housing.

2. The antenna assembly of claim 1, wherein the first locking portion is positioned on an interior surface of the interior layer and the second locking portion is positioned on an exterior surface of the exterior layer.

3. The antenna assembly of claim 1, wherein one of the first locking portion and second locking portion is a hook fastener, and the other of the first locking portion and the second locking portion is a loop fastener.

4. The antenna assembly of claim 1, wherein the antenna is secured to the interior layer.

5. The antenna assembly of claim 1, wherein the antenna includes a plurality of arms.

6. The antenna assembly of claim 1, wherein the interior and exterior layers are formed of a fabric.

7. The antenna assembly of claim 1, wherein the circuitry housing includes a control panel.

8. The antenna assembly of claim 7, wherein the control panel includes at least one interface button.

9. The antenna assembly of claim 8, wherein a first interface button of the at least one interface button controls at least one neurostimulation setting of a control circuit of the printed circuit board.

10. The antenna assembly of claim 9, wherein the at least one neurostimulation setting includes at least one of: an amplitude setting, a pulse width setting, a frequency setting, and a preset program setting.

11. The antenna assembly of claim 1, further comprising a battery charging port.

12. The antenna assembly of claim 1, wherein the band is stretchable such that it will expand when wrapped around a user's body, and once removed from the user's body will return to its original shape.

13. The antenna assembly of claim 1, wherein the band is part of a hem of an article of clothing.

14. The antenna assembly of claim 1, wherein one of the first surface irregularity and the second surface irregularity is a projection, and the other of the first surface irregularity and the second surface irregularity is a recess.

15. The antenna assembly of claim 1, wherein the connector is a coaxial cable.

16. The antenna assembly of claim 1, further comprising an alarm.

17. The antenna assembly of claim 16, wherein the alarm is a piezo alarm.

18. An antenna assembly comprising:
   a band including an interior fabric layer and an exterior fabric layer, and configured to be wrapped around a portion of a user's body such that the interior fabric layer faces a user's body;
   a locking assembly including a first locking portion and a second locking portion, one of the first locking portion and the second locking portion being a hook fastener, and the other of the first locking portion and the second locking portion being a loop fastener;
   an antenna positioned between the interior and the exterior layers;
   a docking port positioned between the interior and the exterior layers;
   a circuitry housing received in the docking port and having an interior cavity:
   a printed circuit board including a control circuit and seated in the interior cavity of the circuitry housing;
   an alarm seated in the interior cavity of the circuitry housing;
   a battery seated in the interior cavity of the circuitry housing;
   a control panel positioned at an open end of the interior cavity of the circuitry housing and having a plurality of interface buttons to control at least one of: an amplitude setting, a pulse width setting, a frequency setting, and a preset programs setting;
   a connector having a first end connected to the printed circuit board and a second end connected to the antenna;

a first surface irregularity on an interior surface of the docking port; and a mating second surface irregularity on an exterior surface of the circuitry housing.

19. An antenna assembly comprising:
a band including an interior stretchable layer and an exterior stretchable layer, and configured to be wrapped around a portion of a user's body such that the interior stretchable layer faces a user's body;
a locking assembly including a hook fastener on one of the interior stretchable layer and the exterior stretchable layer and a loop fastener on the other of the interior stretchable layer and the exterior stretchable layer;
an antenna including a plurality of arms and positioned between the interior and exterior stretchable layers;
a docking port positioned between the interior and the exterior layers, a first surface irregularity being formed on an interior surface of the docking port;
a circuitry housing received in the docking port, and having a base, a cover secured to the base, a mating second surface irregularity formed on an exterior surface of the circuitry housing, and an interior cavity;
a printed circuit board including a control circuit and seated in the interior cavity of the circuitry housing;
a piezo alarm seated in the interior cavity of the circuitry housing;
a rechargeable battery having a charging port and seated in the interior cavity of the circuitry housing;
a control panel positioned at an open end of the interior cavity of the circuitry housing and having a plurality of interface buttons to control at least one of: an amplitude setting, a pulse width setting, a frequency setting, and a preset programs setting;
a connector having a first end connected to the printed circuit board and a second end connected to the antenna;
a first surface irregularity on an interior surface of the docking port; and
a mating second surface irregularity on an exterior surface of the circuitry housing.

* * * * *